United States Patent [19]

Krawchuk

[11] Patent Number: 4,716,767

[45] Date of Patent: Jan. 5, 1988

[54] RUPTURE TESTING APPARATUS FOR BOILER TUBES

[75] Inventor: Myron Krawchuk, Newton, N.J.

[73] Assignee: Foster Wheeler Energy Corporation, Clinton, N.J.

[21] Appl. No.: 848,617

[22] Filed: Apr. 7, 1986

[51] Int. Cl.$^4$ .................................................. G01N 3/54
[52] U.S. Cl. ..................................... 73/834; 73/865.6
[58] Field of Search ............... 73/826, 831, 834, 837, 73/838, 840, 865.6; 374/49

[56] References Cited

U.S. PATENT DOCUMENTS

| | | | |
|---|---|---|---|
| 2,942,455 | 6/1960 | Smith | 73/837 X |
| 3,135,106 | 6/1964 | Lazan | 374/49 |
| 3,934,464 | 1/1976 | McCauley | 73/837 X |

OTHER PUBLICATIONS

Chun, J. S. et al., Chemical Vapor . . . Temperatures, J. Electrochem. Soc., vol. 118, No. 9, Sep. 1971, pp. 1492–1498.

Primary Examiner—Jerry W. Myracle
Attorney, Agent, or Firm—Marvin A. Naigur; Warren B. Kice

[57] ABSTRACT

A boiler tube rupture testing apparatus and method in which two segments are inserted into a tube section which sections together form a disc having a outer diameter slightly less than the inner diameter of the tube section. A creep rupture machine is connected to the individual segments for exerting to oppositely directed forces on the segments, respectively. The forces can be selected to simulate the hoop stress applied to the tube section due to internal pressure and can be maintained on the tube section until rupture occurs which will lead to as accurate estimation of the life of the tube.

2 Claims, 2 Drawing Figures

RUPTURE TESTING APPARATUS FOR BOILER TUBES

BACKGROUND OF THE INVENTION

This invention relates to a rupture testing apparatus for boiler tubes and more particularly to such an apparatus for determining the approximate remaining life of a boiler tube by subjecting it to a hoop stress rupture test.

Two basic methods have been used to date to estimate the remaining life of a tube subjected to internal pressure, such as a boiler tube that carriers water and/or steam at relatively high pressures. The first method utilizes sections of a representative tube subjected to operating pressure and elevated temperatures to accelerate the creep stress to which the tube is subjected. However due to the length required for the test specimens the tubes may have to be removed from an area which had not been exposed to the same degradation of properties if the boiler section in question had experienced a very localized area of distress. Also, due to boiler design considerations, i.e. bends, welds, brackets, etc., a sufficient sample tube length may not be available. Also it is difficult to run multiple tests at high pressures and temperatures rendering the tests more expensive. Further, the metallurgical samples may have to be taken a distance from the critical area in question and may not be representative of this area.

A second method of estimating the remaining life of a tube involves the use of miniature cordal tensile specimens machined from thick wall tubes. However, this is a uniaxial test and since most tube damage initiates near the surface the initial damage may be machined away in preparing this type of specimen. Also, since the relatively small cross sectional area and newly machined surfaces are exposed to atmosphere, the resulting higher oxidation rates could have a significant affect on the test results. Further, the specimens cannot be manufactured from thin wall tubes.

SUMMARY OF THE INVENTION

It is therefore an object of the present invention to provide a rupture testing apparatus and method which requires a minimum length of tube for specimens and in which the specimens are relative inexpensive to manufacture.

It is a further object of the present invention to provide an apparatus and method of the above type in which the full wall thickness of the tube specimen is utilized which will minimize excessive oxidation and maintain prototypical conditions.

It is a still further object of the present invention to provide a apparatus and method of the above type in which the metallurgical sample can be taken in close proximity to the distressed area which will yield data that is more representative.

It is a still further object of the present invention to provide an apparatus and method of the above type which can be used on most tubes and materials in present steam generator environments.

Toward the fulfillment of these and other objects the present invention features the use of two segments which together form a disc having a outer diameter slightly less than the inner diameter of the tube section for insertion into the tube section. A creep rupture machine is connected to the individual segments for exerting two oppositely directed forces on the segments, respectively. The forces can be selected to simulate the hoop stress applied to the tube section due to internal pressure and can be maintained on the tube section until rupture occurs, which will lead to a fairly accurate estimation to the life of the tube.

BRIEF DESCRIPTION OF THE DRAWINGS

The above brief description as well as further objects, features and advantages of the present invention will be more fully appreciated by reference to the following detailed description of presently preferred but nonetheless illustrative embodiments in accordance with the present invention when taken in conjunction with the accompanying drawings wherein.

DESCRIPTION OF THE PREFERRED EMBODIMENTS

Figure 1:
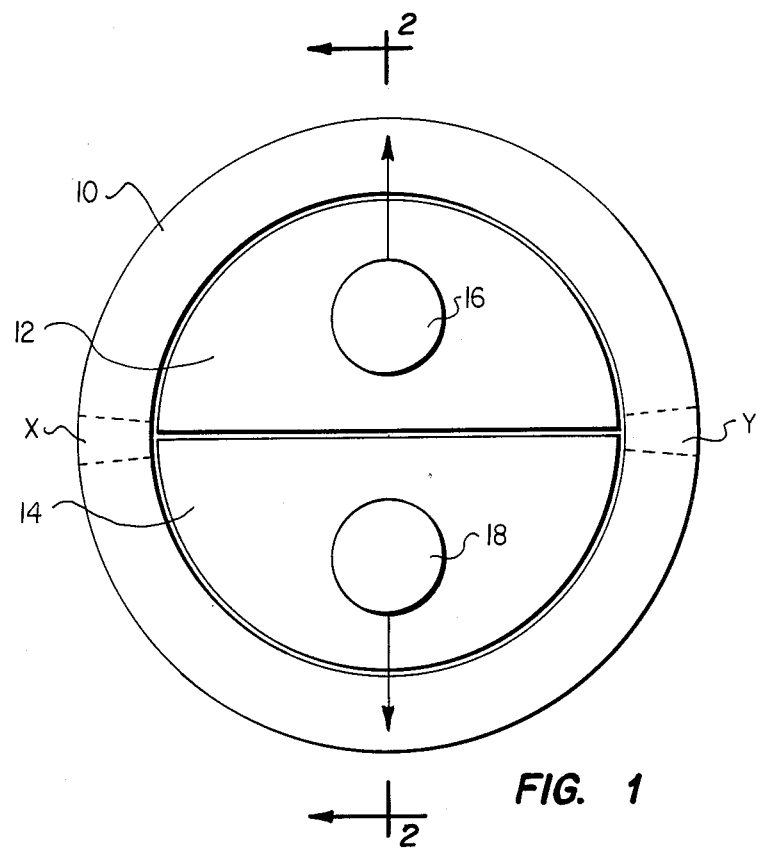
FIG. 1 is a cross sectional view depicting the testing apparatus of the present invention shown installed in a tube section to be tested.

Referring specifically to the drawings, the reference numeral 10 refers, in general, to a tube section which is to be tested according to the present invention and which has a relative short length $\frac{5}{8}''$ to $1''$).

Figure 2:
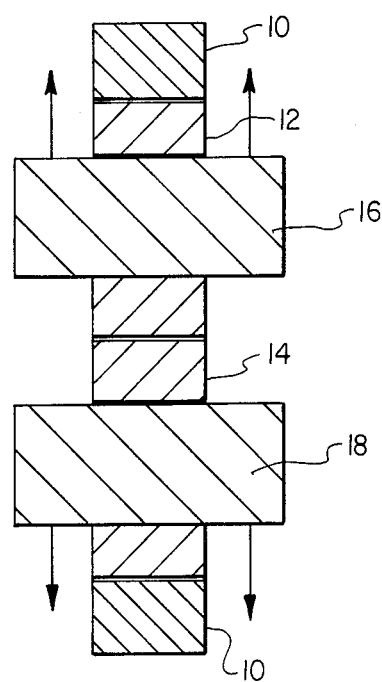
FIG. 2 is a cross sectional view taken along the line 2-2 of FIG. 1.

Two loading segments 12 and 14 are inserted within the tube section 10 and are of semicircular shape so that they together form a disc having an external diameter slightly less than the internal diameter of the tube section 10. As shown in FIG. 2, the thickness of the disc formed by the segments 12 and 14 corresponds to the length of the tube section 10.

A pair of rods, or dowels, 16 and 18 extend through the segments 12 and 14, respectively, and project outwardly from the opposed faces of the segments parallel to the axis of the disc formed by the segments. The dowels 16 and 18 are sized so that they can be connected to a conventional creep rupture machine in a conventional manner so that forces can be exerted on the dowels, and therefore the segments 12 and 14, in opposite directions as shown by the arrows in FIG. 1 and 2.

According to the present invention, the segments 12 and 14 are inserted within the tube section 10 to be tested, and the dowels 16 and 18 are connected to a creep rupture machine (not shown). The wall thickness and width of the tube section 10 are determined and recorded, and the required tensile force to rupture the tube is calculated based on a standard formula. The creep rupture machine is then actuated to exert the latter forces on the segments 12 and 14, and therefore on the interior of the tube section 10, in opposite directions to simulate a typical tangential hoop stress located approximately at the areas designated by the reference letters X and Y in FIG. 1. The forces applied by the creep rupture machine are maintained until the tube section 10 in fact ruptures.

It is understood that the foregoing procedure is done under carefully controlled temperatures and that, according to a preferred embodiment, the tests are conducted at temperatures above the anticipated service temperature and, upon rupture, the actual remaining life is estimated on a temperature vs. time-to-rupture plot by extrapolating to the service temperature.

Several advantages result from the technique of the present invention. For example, a minimum length of tube section is required and the section itself is inexpensive to manufacture. Also, the full wall thickness of the specimen is utilized which minimizes excessive oxidation and maintains prototypical conditions. Further, the close proximity of the test sample to the distressed area will yield data that is more representative, especially if the distressed area of the tube is extremely limited.

A latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention therein.

What is claimed is:

1. A rupture testing apparatus for a tube section, said apparatus comprising two segments each having a semicircular cross section, said segments together forming a disc having an outer diameter slightly less than the inner diameter of said tube section for insertion into said tube section, and two spaced parallel dowels extending through said two segments, respectively, and projecting from the opposed faces of said segments, respectively, and means operatively engaging the projecting portion of said dowels for applying oppositely directed tensile forces to said respective segments to simulate the hoop stress applied to said tube due to internal pressure.

2. The apparatus of claim 1 wherein the thickness of said disc substantially corresponds to the length of said tube section.

* * * * *